United States Patent
Johs et al.

(10) Patent No.: US 8,467,057 B1
(45) Date of Patent: *Jun. 18, 2013

(54) ELLIPSOMETERS AND POLARIMETERS COMPRISING POLARIZATION STATE COMPENSATING BEAM DIRECTING SAMPLE WOBBLE COMPENSATING SYSTEM, AND METHOD OF USE

(75) Inventors: Blaine D. Johs, Lincoln, NE (US); Ping He, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/200,413

(22) Filed: Sep. 23, 2011

Related U.S. Application Data

(63) Continuation-in-part of application No. 12/584,795, filed on Sep. 12, 2009, now Pat. No. 8,339,602, and a continuation-in-part of application No. 12/587,190, filed on Oct. 2, 2009, now Pat. No. 8,339,603.

(60) Provisional application No. 61/191,988, filed on Sep. 15, 2008, provisional application No. 61/195,068, filed on Oct. 3, 2008, provisional application No. 61/403,996, filed on Sep. 25, 2010.

(51) Int. Cl.
*G01J 4/00* (2006.01)
(52) U.S. Cl.
USPC .......................................................... 356/369
(58) Field of Classification Search
None
See application file for complete search history.

(56) References Cited

U.S. PATENT DOCUMENTS

| | | | | |
|---|---|---|---|---|
| 3,353,894 A * | 11/1967 | Harris | ............................ | 359/317 |
| 3,360,323 A * | 12/1967 | Weisman et al. | ........ | 359/484.05 |
| 3,449,039 A * | 6/1969 | Hoffman, Jr. | ............ | 359/489.09 |
| 3,449,576 A * | 6/1969 | Lipp et al. | ................ | 359/489.11 |
| 3,463,571 A * | 8/1969 | Boehm et al. | ............ | 359/489.09 |
| 3,841,758 A * | 10/1974 | Gievers | ......................... | 356/459 |
| 5,517,312 A | 5/1996 | Finarov | ........................ | 356/630 |
| 5,929,995 A | 7/1999 | Johs et al. | ..................... | 356/369 |
| 5,963,327 A | 10/1999 | He et al. | ......................... | 356/369 |
| 5,969,818 A | 10/1999 | Johs et al. | ..................... | 356/369 |
| 6,034,777 A | 3/2000 | Johs et al. | ..................... | 356/369 |
| 6,549,282 B1 | 4/2003 | Johs et al. | ..................... | 356/369 |
| RE38,153 E | 6/2003 | Finarov | ........................ | 356/630 |
| 6,804,004 B1 | 10/2004 | Johs et al. | ..................... | 356/369 |

(Continued)

FOREIGN PATENT DOCUMENTS

| | | | |
|---|---|---|---|
| DE | 19721044 A1 * | 11/1998 | |
| JP | 04074934 A * | 3/1992 | |
| JP | 04198928 A * | 7/1992 | |

OTHER PUBLICATIONS

Haberland et al. "Ellipsometer and Reflectance—Amjo—Tropy Measurements on Rotating Samples", Thin Solid Films, 313-354 (1998) 620-624.

*Primary Examiner* — Gordon Stock, Jr.
(74) *Attorney, Agent, or Firm* — James D. Welch

(57) ABSTRACT

An improved system and method for investigation of a wobbling surface of a sample with an electromagnetic beam, involving application of a beam directing dual reflection surface "prism" system, which, while effecting beam locus direction rotation of 90 degrees also preserves beam polarization state. The system allows causing an electromagnetic beam to access an otherwise difficult to access sample in, for instance, a vacuum deposition chamber, and enables achieving very closely spaced incident and spherical mirror reflected points of beam reflection from a sample surface in use.

19 Claims, 3 Drawing Sheets

U.S. PATENT DOCUMENTS

| | | | |
|---|---|---|---|
| 7,277,171 B1 | 10/2007 | Johs et al. | 356/369 |
| 7,283,218 B2 * | 10/2007 | Zettler | 356/43 |
| 7,489,399 B1 * | 2/2009 | Lee | 356/369 |
| 2002/0027936 A1 * | 3/2002 | Govorkov et al. | 372/57 |
| 2004/0070760 A1 | 4/2004 | Stehle et al. | |
| 2011/0090501 A1 * | 4/2011 | Mamin et al. | 356/364 |

* cited by examiner

ELLIPSOMETERS AND POLARIMETERS COMPRISING POLARIZATION STATE COMPENSATING BEAM DIRECTING SAMPLE WOBBLE COMPENSATING SYSTEM, AND METHOD OF USE

This Application is a CIP of application Ser. No. 12/584,795, Filed Sep. 12, 2009 now U.S. Pat. No. 8,339,602 and Ser. No. 12/587,190, Filed Oct. 2, 2009 now U.S. Pat. No. 8,339,603 which Claim benefit of Provisional 61/191,988 Filed Sep. 15, 2008 and 61/195,068 Filed Oct. 3, 2008 respectively, and directly Claims benefit from Provisional Application 61/403,996, Filed Sep. 25, 2010.

TECHNICAL FIELD

The present invention relates to the reduction of distortions in electromagnetic radiation spectra obtained from investigation of rotating samples caused by sample surface precession "wobble", and more particularly to an improved system, and method for reducing the effects of sample wobble during investigation of a precessing surface thereof with an electromagnetic beam, said system and method involving application of a beam directing dual reflection surface "prism" which preserves polarization state of a polarized beam of electromagnetic radiation interacting therewith.

BACKGROUND

A paper by Haberland et al. titled: "Elllpsometer and Reflectance-Anisotropy Measurements on Rotating Samples", Thin Solid Films, 313-314, (1998) 620-624, describes a method for significantly reducing signal wobble when ellipsometry is performed on rotating samples, the surfaces of which are not oriented normal to the axis of rotation. This paper discloses that placing a spherical mirror in a Spectroscopic Ellipsometer so that it intercepts a beam of electromagnetic radiation that has reflected from a rotating sample surface, and directs it back onto said rotating sample surface so that it again reflects therefrom before entering a detector, serves to reduce distortions in ellipsometric signal spectra caused by said sample wobble.

Also disclosed, because they disclose beam directing means that operate based on Total Internal Reflection or on Specular reflection, are U.S. Pat. Nos. 6,034,777, 6,549,282 and 6,804,004 to Johs et al. which describe methodology for correcting polarizations state effects introduced by beam directing means that rely on specular reflection so that uncorrelated PSI and DELTA of a Sample being investigated can be achieved. Further, U.S. Pat. No. 5,969,818 to Johs et al. describes a four bounce mirror system which performs orthogonal component compensation, and U.S. Pat. No. 5,953,327 to He et al. and Published Application US 2004/0070760 by Stehle et al. describe an ellipsometer or the like in which beam directing means allow a source and detector to be positioned side by side rather than distally from one another along the locus of a sample investigating beam. Further, U.S. Pat. No. 5,929,995 to Johs describes use of beam directing prisms in a vacuum chamber, thereby allowing an electromagnetic beam to reach otherwise an otherwise inaccessible sample therein, no known reference teaches application of the dual reflective surface system which is subject in this disclosure to enable investigation of a rotating sample surface, which surface demonstrates precession in, for instance, an in-situ sample processing apparatus.

No known reference however, discloses, in the context of an ellipsometer or polarimeter system, a dual reflection surface (eg. a prism system, configured to provide a polarized output beam, the locus of which is rotated in direction by 90 degrees, (eg. in a "X"-"Z" plane effected by re-directing an input beam which enters thereinto along a "Y" axis, in an "X"-"Y"-"Z" coordinate system), wherein the second reflection substantially compensates effects of the first, as regards beam Polarization State. This is especially true where a polarized beam of electromagnetic radiation is used to investigate a rotating sample that is "wobbling", (ie the rotating sample surface is not oriented normal to the sample rotation axis, so that a precession effect occurs during rotation), and wherein practice of a method of use of the system effectively reduces the effect of angular sample wobble on reflected ellipsometer beam signal spectra.

The references identified above are all incorporated by reference into this Disclosure.

DISCLOSURE OF THE INVENTION

To begin, it is to be understood that, in the following, orthogonal "X"-"Y"-"Z" coordinates will be utilized to aid with description of a present invention system, however, it is to be appreciated that a so described present invention system can be translated and rotated about any of said demonstrative coordinates without altering its operation. Therefore, the present invention is not to be considered limited in any way by the use of demonstrative "X"-"Y"-"Z" coordinates in the description thereof, to orientation in any specific laboratory coordinate system. Further, it is to be understood that the present invention finds a important application in directing polarized electromagnetic beams in a polarization state preserving manner to surfaces of samples which are located in hard to access systems, (such as vacuum deposition systems), particularly where the sample is caused to rotate while data is acquired therefrom using an electromagnetic beam which is caused to reflect therefrom twice, and then enter a detector.

Also, as a primary application of the present invention is in an ellipsometer, polarimeter or the like system, an ellipsometer, polarimeter or the like system will be used as a non-limiting example in this disclosure.

Continuing, the present invention comprises a dual prism means configured to provide a polarized output beam in a "X"-"Z" plane, by re-directing an input beam which enters thereinto along a "Y" axis in an orthogonal "X"-"y"-"Z" coordinate system. Said dual prism means further provides benefit in that it substantially compensates any effects on polarization state of a polarized beam of electromagnetic radiation entered by a interaction with a first beam directing reflection therewithin, by the effects of interaction with a second beam directing reflection therewithin, (Note Polarization State basically refers to a relationship between orthogonal p and s components in a polarized beam of electromagnetic radiation). This results because the effect of a first reflection on an orthogonal, (eg. p or s component), of a polarized beam in the dual prism means configuration, is canceled by a similar effect in the second reflection on the other, (eg. s or p component), respectively. For example, if the first reflection has an effect on the p component, the second reflection has a compensating effect on the component and vice-versa. It is noted that the just described compensation occurs as the planes of the reflective surfaces of the dual prism are normal to one another.

It is also disclosed that the reflective surfaces of the dual prism can be coated with a material, (such as aluminum, but not limited to such), and the present invention will still function, but with different physics. Without the coating on the reflective surfaces the reflections are based on total internal reflection. With a coating present the reflective surfaces the reflections are based on specular reflection. In fact, it is to be understood that a system of two specularly reflecting means can replace the dual prisms, if the planes of incidence that a beam makes with respect to said two surfaces are normal to one another, as are the reflective surfaces of the two prisms. When the reflections are specular, polarization state corrections of the effects thereof is described in U.S. Pat. Nos. 6,034,777, 6,549,282 and 6,804,004 to Johs et al. These patents describe methodology for correcting polarizations state effects introduced by beam directing means that rely on specular reflection, so that uncorrelated PSI and DELTA of a Sample being investigated can be achieved.

It is also to be appreciated that the dual prism means can be rotated about an axis parallel to the "Y" axis of the "X"-"Y"-"Z" coordinate system to alter the angle at which the output beam exits therefrom in the "X"-"Z" plane. Typically said rotation will be along the input beam locus which, as mentioned above, can be taken to approach along a "Y" axis. This enables adjusting the angle-of-incidence (AOI) of the exiting beam with respect to a sample positioned so that said output beam impinges thereonto.

More specifically, the present invention is a system for investigating a sample that is caused to rotate about an axis which is not exactly normal to a surface thereof such that said surface "wobbles" as it rotates. Said system comprises:
 a source of a spectroscopic beam of electromagnetic radiation;
 a dual reflection surface means selected from the group consisting of:
  two separate reflection surfaces; and
  a single element having two reflection surfaces;
 configured to provide an output beam in a "X"-"Z" plane, by re-directing an input beam which enters thereinto along a "Y" axis, in an "X"-"Y"-"Z" coordinate system; said first dual reflection surface means further serving to substantially compensate any beam polarization effects on a beam polarization state entered by a first beam directing reflection therewithin, by the effects of a second beam directing reflection therewithin, the mechanism thereof being that the effect of a first reflection on a p or s component of a polarized beam in the dual reflection surface means configuration, is canceled by a similar effect in the second reflection on an s or p component, respectively.

The present invention further comprises a system for causing a sample to rotate about an axis which is not exactly normal to a surface thereof;
 a spherical mirror; and
 a detector.

In use said source of spectroscopic beam of electromagnetic radiation directs a beam of spectroscopic electromagnetic radiation along a "Y" axis such that it enters said dual reflection surface means and exits therefrom in an "X"-"Z" plane such that it reflects from the surface of a sample substantially, but not exactly in an "X"-"Y" plane, and which is caused to rotate about an axis directed parallel to the "Z" axis such that said sample surface "wobbles" as it rotates, and such that said beam of spectroscopic electromagnetic radiation which reflects from a first location on said wobbling sample surface further reflects from said spherical mirror back toward said wobbling sample surface such that is reflects therefrom at a second location thereon and enters said detector.

The second location on said wobbling sample can be directed by reflection from said spherical mirror to be translated along the "X" axis or translated along the "Y" axis.

Said system can further comprise a polarizer between said source and sample, and an analyzer between said sample and detector and in which the system is an ellipsometer or polarimeter, and wherein the effect of the first reflection on a p or s component of a polarized beam in the dual reflection surface means configuration, is canceled by a similar effect in the second reflection on an s or p component, respectively.

In use the "X"-"Y"-"Z" coordinate system can be aligned, or not aligned with laboratory coordinates.

A method investigating a sample which is caused to rotate about an axis which is not exactly normal to a surface thereof such that said surface "wobbles" as it rotates, with electromagnetic beam, said method serving to reduce the effect of said wobble, comprising:
 a) providing a system as described above;
 b) obtaining data from said detector while causing said source of spectroscopic beam of electromagnetic radiation directs a beam of spectroscopic electromagnetic radiation along a "Y" axis such that it enters said dual reflection surface means and exits therefrom in an "X"-"Z" plane such that it reflects from the surface of a sample substantially, but not exactly in an "X"-"Y" plane, and which is caused to rotate about an axis directed parallel to the "Z" axis such that said sample surface "wobbles" as It rotates, and such that said beam of spectroscopic electromagnetic radiation which reflects from a first location on said wobbling sample surface further reflects from said spherical mirror back toward said wobbling sample surface such that is reflects therefrom at a second location thereon and enters said detector.

Said method can further involve, in step a, further providing a polarizer between said source and sample, and an analyzer between said sample and detector and in which the system is an ellipsometer or polarimeter; and wherein during practice of step b, as the beam of spectroscopic electromagnetic radiation passes through said dual reflection surface means, the effect of the first reflection on a p or s component of a polarized beam in the dual reflection surface means configuration, is canceled by a similar effect in the second reflection on an s or p component, respectively.

Said method can Involve the second location on said wobbling sample being directed by reflection from said spherical mirror to be translated along the "X" axis, or along the "Y" axis. Said method can also involve the "X"-"Y"-"Z" coordinate system being aligned with, or not aligned with laboratory coordinates.

A more general recitation is then that a present invention system for investigating a sample which is caused to rotate about an axis which is not exactly normal to a surface thereof such that said surface "wobbles" as it rotates, comprises:
 a source of a spectroscopic beam of electromagnetic radiation;
 a dual reflection surface means selected from the group consisting of:
  two separate reflection surfaces; and
  a single element having two reflection surfaces;
 configured to provide an output beam in a plane which is rotated by 90 degrees from the locus of an input beam entered thereinto; said dual reflection surface means further serving to substantially compensate any beam polarization effects on a beam polarization state entered by a first beam directing reflection therewithin, by the effects of a second beam directing reflection therewithin, the mechanism thereof being that the effect of a first reflection on a p or s component of a polarized beam in the dual reflection surface means configuration, is canceled by a similar effect in the second reflection on an s or p component, respectively;

a system for causing a sample to rotate about an axis which is not exactly normal to a surface thereof;

a spherical mirror; and a detector;

such that said source of spectroscopic beam of electromagnetic radiation directs an input beam of spectroscopic electromagnetic radiation to enter said dual reflection surface means and exit therefrom in a plane which is rotated by 90 degrees from the locus of the input beam such that it reflects from the surface of a sample while it is caused to rotate about an axis which is not normal to said surface of said sample, such that said sample surface "wobbles" as it rotates, and such that said beam of spectroscopic electromagnetic radiation which reflects from a first location on said wobbling sample surface further reflects from said spherical mirror back toward said wobbling sample surface such that is reflects therefrom at a second location thereon and enters said detector.

Said system can further comprises a polarizer between said source and sample, and an analyzer between said sample and detector and in which the system is an ellipsometer or polarimeter, and wherein the effect of the first reflection on a p or s component of a polarized beam in the dual reflection surface means configuration, is canceled by a similar effect in the second reflection on an s or p component, respectively.

A method Investigating a sample which is caused to rotate about an axis which is not exactly normal to a surface thereof such that said surface "wobbles" as it rotates, with electromagnetic beam, said method serving to reduce the effect of said wobble, comprising:

a) providing a system as described just above; and b) obtaining data from said detector while causing said source of spectroscopic beam of electromagnetic radiation directs a beam of spectroscopic electromagnetic radiation along an axis such that it enters said dual reflection-surface means and exits therefrom in a plane which is rotated by 90 degrees, such that it reflects from the surface of a sample which is caused to rotate about an axis not directed normal to the surface of said sample such that said sample surface "wobbles" as it rotates, and such that said beam of spectroscopic electromagnetic radiation which reflects from a first location on said wobbling sample surface further reflects from said spherical mirror back toward said wobbling sample surface such that is reflects therefrom at a second location thereon and enters said detector.

Said method can also include, in step a, further providing a polarizer between said source and sample, and an analyzer between said sample and detector and in which the system is an ellipsometer or polarimeter; and wherein during practice of step b, as the beam of spectroscopic electromagnetic radiation passes through said dual reflection surface means, the effect of the first reflection on a p or s component of a polarized beam in the dual reflection surface means configuration, is canceled by a similar effect in the second reflection on an s or p component, respectively.

Further, methodology of practicing the present Invention can further include at least one selection from the group consisting of:

storing at least some data provided by said data detector in machine readable media;

analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which Is applied to provide a concrete and tangible result; and analyzing at least some of the data provided by said data detector and causing at least some thereof to produce a signal which is applied to provide a concrete and tangible result.

Finally, it should be appreciated that the present invention allows achieving a very small spacing between where the beam from the prism, and the beam reflected from the spherical mirror impinge on a wobbling sample. This allows near elimination of the beam precession in the output beam that enters the detector. Testing on an ex-situ system demonstrated that the return beam path reduced beam precession from about 25 mm to <1 mm for a +/−0.8° substrate wobble and a 2 m beam path, reducing the signal intensity variation from 100% to <2%. This provided very good agreement between data obtained from rotating and stationary samples.

The present invention will be better understood by reference to the Detailed Description Section of this Specification, in combination with the Drawings.

DETAILED DESCRIPTION

At the outset of this section, it is emphasized that in the following "X"-"Y"-"Z" coordinates are used to help describe the present invention. This is done for convenience in making the invention clear. However, it is not to be considered that the presenting invention is in any way dependent thereupon.

Figure 1:
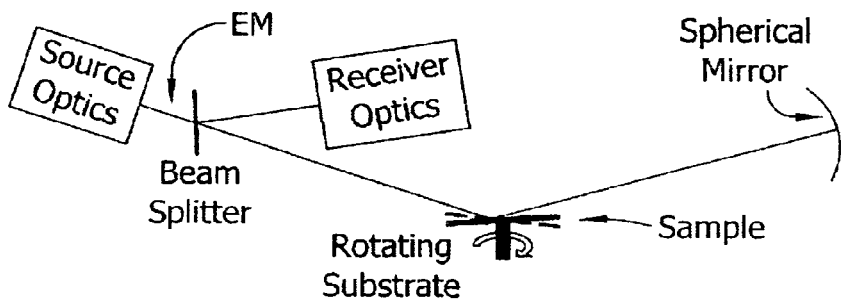
FIG. 1 shows a prior art approach to minimizing the effect of rotating sample wobble on measurements obtained using electromagnetic radiation.

Continuing, FIG. 1 shows a prior art approach to minimizing the effect of rotating sample wobble on measurements obtained using electromagnetic radiation. Note that a beam of electromagnetic radiation (EM) is directed from a Source Optic to pass through a Beam Splitter, reflect from a Sample on a Rotating Stage, then proceed to and reflect from a Spherical Mirror back onto the Rotating Sample and via the effect of said Beam Splitter enter Receiver Optics. This basic procedure is successful in reducing the effect of rotating sample wobble. The present invention uses a similar approach to reducing the effect of rotating sample wobble as regards beam trajectory, but applies a prism system.

Figure 2A:
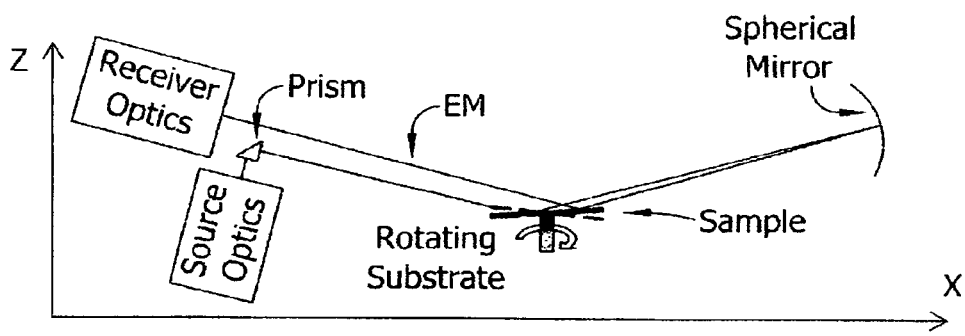
FIGS. 2a, 2b, 3a and 3b show two embodiments of the present invention.
Figure 2B:
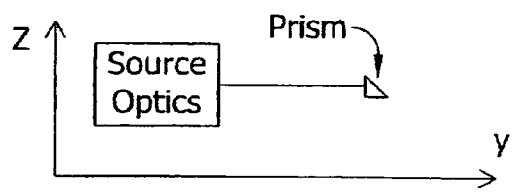
Figure 3A:
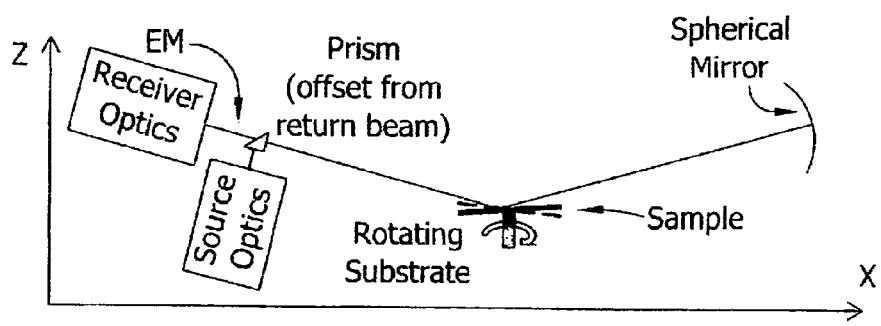
Figure 3B:
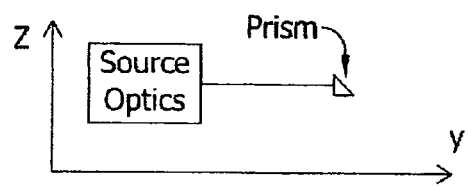

FIGS. 2a and 3a are directed to the present invention and are to be viewed in the context of an orthogonal "X"-"Y"-"Z" coordinate system which provides that the "X" axis projects to the right, the "Z" axis projects upward and the "Y" axis projects into the paper. FIG. 2a then shows a first embodiment of the present invention system wherein a beam of electromagnetic radiation is directed from a Source (Optics) along a "Y" axis, (ie. In/out of the paper, (see FIG. 2b). That is, the Source Optics in FIG. 3a Is to be viewed as a two-dimensional representation of a three-dimensional system that provides a beam in a plane parallel to "Z"-"Y" coordinates), so that it enters a dual reflection surface means (eg. Prism), (see FIGS. 4 and 5 for better three-dimensional insight thereto), and Is directed thereby Into an "X"-"Z" plane so that it impinges on a First location on a surface of a substrate at an angle-of-incidence thereto. The substrate is shown as being caused to rotate about a rod which Is oriented parallel to a "Z" axis. Note, however, that the surface of said substrate is not to be considered as exactly being in an "X"-"Y" plane, so wobbles as it is rotated. The beam of electromagnetic radiation then reflects from a Spherical Mirror back onto the surface of the rotating substrate at a Second location thereon which translated along the "X" axis from the first location. The beam of electromagnetic radiation then enters a Detector. FIGS. 3a and 3b are similar to FIGS. 2a and 2b except that the Second location on the surface of the substrate is translated in a direction parallel to the "Y" axis from the First location.

Figure 4:
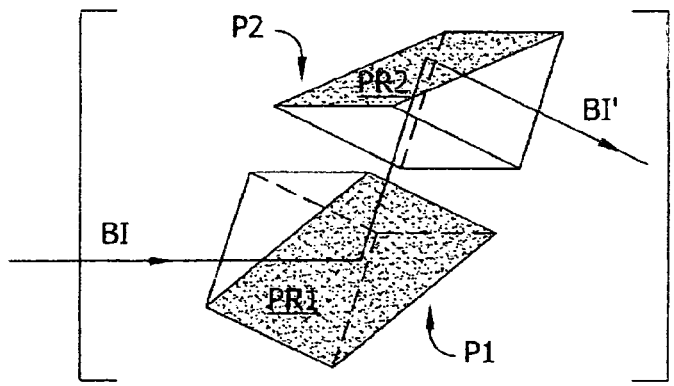
FIGS. 4-6 show two element, and integrated element embodiments, respectively, of a dual reflection surface means identified as Prism in FIGS. 1 and 2.
Figure 5:
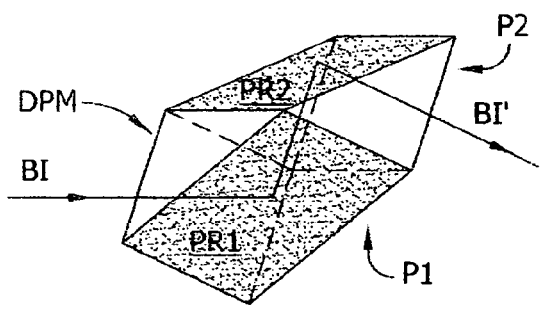

FIGS. 4 and 5 show two element, and integrated element embodiments, respectively, of the dual reflection surface means (eg. identified as Prism in FIGS. 2 and 3). Note that there is a First reflecting surface (PR1) and a Second reflecting surface (PR2), said (PR1) and (PR2} being oriented at ninety (90) degrees to one another such that a beam (BI) entered along a "Y" axis exits in an "X"-"Z" plane as viewed in an orthogonal coordinate system.

Figure 6:
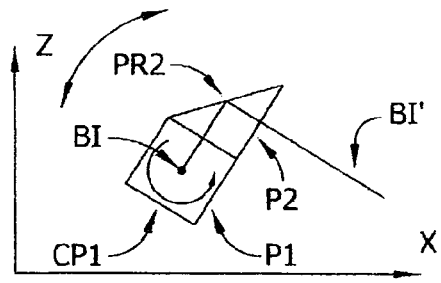

FIG. 6 Is included to show a front elevational view of the system in FIGS. 4 and 5, wherein a beam (BI) enters along a "Y" axis, (eg, Into the page), and exits as (BI'} in an "X"-"Z" plane. The demonstration of the "X"-"Y"-"Z" orthogonal axes in FIG. 6, as regards the FIGS. 4 and 5 dual reflection surfaces (PR1) (PR2) serves to correlate to FIGS. 2a and 3a, which are also front elevational.

Use of a Prism as in FIGS. 4-6 in a system as in FIGS. 2a and 3a allows keeping outgoing and return beams very close to one another. This aspect of the present Invention is the primary focus thereof, and is considered new, novel and non-obvious in a sample wobble compensation system and method.

Figure 7:
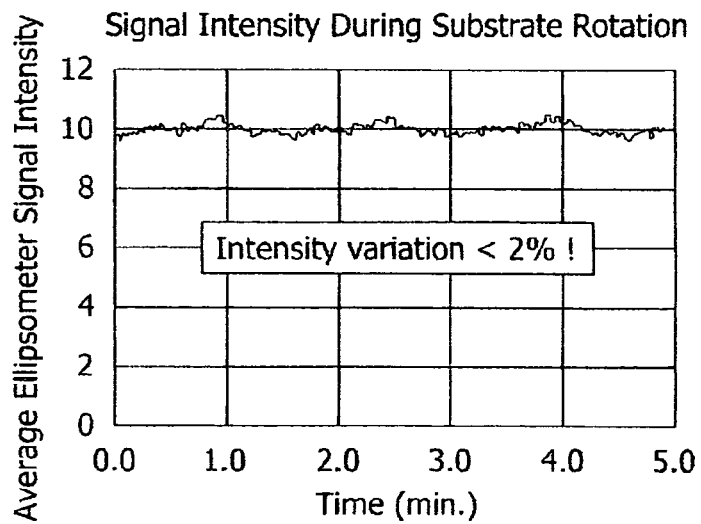
FIG. 7 shows that the present invention provides excellent compensation of the effect of rotating sample wobble.

Finally, FIG. 7 shows that the present invention provides excellent compensation of the effect of rotating sample wobble. Note that the wobble effect is about 2%.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system which comprises a dual reflection surface means selected from the group consisting of:
   first and second separate reflection surfaces; and
   a single element having first and second reflection surfaces;
configured to provide an output beam in an X-Z plane, by re-directing an input beam which enters thereinto along a Y axis, in an X-Y-Z axis coordinate system; said dual reflection surface means further serving to substantially compensate any effects on beam polarization state entered by a first beam directing reflection therewithin, by effects of a second beam directing reflection therewithin, a mechanism thereof being that an effect of the first reflection on a p or s component of a polarized beam in the dual reflection surface means configuration, is canceled by a similar effect in the second reflection on an s or p component, respectively;
said dual reflection surface means being characterized in that projected planes of the first and second reflection surfaces thereof simultaneously:
   intersect the Y and Z axes, but not the X axis, at a single point, and
   intersect the X and Z axes, but not the Y axis, at a single point,
respectively, and in that said second reflection surface is translated from the first reflection surface along the Z axis, as said dual reflection surface means is viewed in frontal elevation, in which the dual reflection surface means is mounted to allow rotation about an axis parallel to the Y axis of the X-Y-Z axis coordinate system to alter an angle at which the output beam exits therefrom.

2. A system as in claim 1, in which said rotation is along an input beam locus, which enables adjusting an angle-of-incidence (AOI) of an exiting beam with respect to a sample positioned so that said output beam impinges thereonto.

3. A system for investigating a sample which is caused to rotate about an axis which is not exactly normal to a surface thereof such that said surface wobbles as said sample rotates, said system comprising:
   a source of a spectroscopic beam of electromagnetic radiation;
   a dual reflection surface means selected from the group consisting of:
      two separate reflection surfaces; and
      a single element having two reflection surfaces;
   configured to provide an output beam in an X-Z plane, by re-directing an input beam which enters thereinto along a Y axis, in an X-Y-Z axis coordinate system; said dual reflection surface means further serving to substantially compensate any beam polarization effects on a beam polarization state entered by a first beam directing reflection therewithin, by effects of a second beam directing reflection therewithin, a mechanism thereof being that an effect of the first reflection on a p or s component of a polarized beam in the dual reflection surface means configuration, is canceled by a similar effect in the second reflection on an s or p component, respectively;
   a system for causing a sample to rotate about an axis which is not exactly normal to a surface thereof;
   a spherical mirror; and
   a detector;
such that said source of a spectroscopic beam of electromagnetic radiation directs a spectroscopic beam of electromagnetic radiation along a Y axis such that said spectroscopic beam of electromagnetic radiation enters said dual reflection surface means and exits therefrom in an X-Z plane such that said spectroscopic beam of electromagnetic radiation reflects from the surface of a sample substantially, but not exactly in an X-Y plane, and which is caused to rotate about an axis directed parallel to the Z axis such that said sample surface wobbles as said sample rotates, and such that said spectroscopic beam electromagnetic radiation which reflects from a first location on said wobbling sample surface further reflects from said spherical mirror back toward said wobbling sample surface such that said spectroscopic beam of electromagnetic radiation reflects therefrom at a second location thereon and enters said detector.

4. A system for investigating a sample as in claim 3, in which the second location on said wobbling sample is directed by reflection from said spherical mirror to be translated perpendicular to the Y axis.

5. A system for investigating a sample as in claim 3, in which the second location on said wobbling sample is directed by reflection from said spherical mirror to be translated along the Y axis.

6. A system for investigating a sample as in claim 3, which further comprises a polarizer between said source and sample, and an analyzer between said sample and detector and in which the system for investigating a sample is an ellipsometer or polarimeter, and wherein an effect of the first reflection on a p or s component of a polarized beam in the dual reflection surface means configuration, is canceled by a similar effect in the second reflection on an s or p component, respectively.

7. A system for investigating a sample as in claim 3, in which the X-Y-Z coordinate system is not aligned with laboratory coordinates.

8. A system for investigating a sample as in claim 3, in which the X-Y-Z coordinate system is aligned with laboratory coordinates.

9. A method of investigating a sample which is caused to rotate about an axis which is not exactly normal to a surface thereof such that said surface wobbles as said sample rotates, with an electromagnetic beam, said method serving to reduce an effect of said wobble, comprising:
 a} providing a system for investigating a sample which is caused to rotate about an axis which is not exactly normal to a surface thereof such that said surface wobbles as said sample rotates, said system comprising:
  a source of a spectroscopic beam of electromagnetic radiation;
  a dual reflection surface means selected from the group consisting of:
   two separate reflection surfaces; and
   a single element having two reflection surfaces;
 configured to provide an output beam in an X-Z plane, by re-directing an input beam which enters thereinto along a Y axis, in an X-Y-Z axis coordinate system; said dual reflection surface means further serving to substantially compensate any beam polarization effects on a beam polarization state entered by a first beam directing reflection therewithin, by effects of a second beam directing reflection therewithin, a mechanism thereof being that an effect of the first reflection on a p or s component of a polarized beam in the dual reflection surface means configuration, is canceled by a similar effect in the second reflection on an s or p component, respectively;
  a system for causing a sample to rotate about an axis which is not exactly normal to a surface thereof;
  a spherical mirror; and
  detector;
such that said source of a spectroscopic beam of electromagnetic radiation directs a spectroscopic beam of electromagnetic radiation along a Y axis such that said spectroscopic beam of electromagnetic radiation enters said dual reflection surface means and exits therefrom in an X-Z plane such that said spectroscopic beam of electromagnetic radiation reflects from the surface of a sample substantially, but not exactly in an X-Y plane, and which is caused to rotate about an axis directed parallel to the Z axis such that said sample surface wobbles as said sample rotates, and such that said spectroscopic beam of electromagnetic radiation which reflects from a first location on said wobbling sample surface further reflects from said spherical mirror back toward said wobbling sample surface such that said spectroscopic beam of electromagnetic radiation reflects therefrom at a second location thereon and enters said detector;
b) obtaining data from said detector while causing said source of spectroscopic beam of electromagnetic radiation to direct a spectroscopic beam of electromagnetic radiation along a Y axis such that said spectroscopic beam of electromagnetic radiation enters said dual reflection-surface means and exits therefrom in an X-Z plane such that said spectroscopic beam of electromagnetic radiation reflects from the surface of a sample substantially, but not exactly in the X-Y plane, and which is caused to rotate about an axis directed parallel to the Z axis such that said sample surface wobbles as said sample rotates, and such that said spectroscopic beam of electromagnetic radiation which reflects from a first location on said wobbling sample surface further reflects from said spherical mirror back toward said wobbling sample surface such that said spectroscopic beam of electromagnetic radiation reflects therefrom at a second location thereon and enters said detector.

10. A method as in claim 9, in which step a) further comprises providing a polarizer between said source and sample, and an analyzer between said sample and detector and in which the system for investigating a sample is an ellipsometer or polarimeter; and wherein during practice of step b), as the spectroscopic beam of electromagnetic radiation passes through said dual reflection surface means, the effect of the first reflection on a p or s component of a polarized beam in the dual reflection surface means configuration, is canceled by a similar effect in the second reflection on an s or p component, respectively.

11. A method as in claim 9, in which the second location on said wobbling sample is directed by reflection from said spherical mirror to be translated in the direction of the spectroscopic beam of electromagnetic radiation.

12. A method as in claim 9, in which the second location on said wobbling sample is directed by reflection from said spherical mirror to be translated along the Y axis.

13. A method as in claim 9, in which the X-Y-Z coordinate system is not aligned with laboratory coordinates.

14. A method as in claim 9, in which the X-Y-Z coordinate system is aligned with laboratory coordinates.

15. A system for investigating a sample which is caused to rotate about an axis which is not exactly normal to a surface thereof such that said surface wobbles as said sample rotates, said system comprising:
 a source of a spectroscopic beam of electromagnetic radiation;
 a dual reflection surface means selected from the group consisting of:
  two separate reflection surfaces; and
  a single element having two reflection surfaces;
 configured to provide an output beam in a plane which is rotated by 90 degrees from a locus of an input beam entered thereinto; said dual reflection surface means further serving to substantially compensate any beam polarization effects on a beam polarization state entered by a first beam directing reflection therewithin, by effects of a second beam directing reflection therewithin, a mechanism thereof being that an effect of a first reflection on a p or s component of a polarized beam in the dual reflection surface means configuration, is canceled by a similar effect in the second reflection on an s or p component, respectively;
 a system for causing a sample to rotate about an axis which is not exactly normal to a surface thereof;
 a spherical mirror; and
 a detector;
such that said source of a spectroscopic beam of electromagnetic radiation directs an input spectroscopic beam of electromagnetic radiation to enter said dual reflection surface means and exit therefrom in a plane which is rotated by 90 degrees from the locus of the input beam such that the spectroscopic beam of electromagnetic radiation reflects from the surface of a sample while said sample is caused to rotate about an axis which is not normal to said surface of said sample, such that said sample surface wobbles as said sample rotates, and such that said spectroscopic beam of electromagnetic radiation which reflects from a first location on said wobbling sample surface further reflects from said spherical mirror back toward said wobbling sample surface such that said spectroscopic beam of electromagnetic radiation reflects therefrom at a second location thereon and enters said detector.

16. A system for investigating a sample as in claim 15, which further comprises a polarizer between said source and sample, and an analyzer between said sample and detector and in which the system for investigating a sample is an ellipsometer or polarimeter, and wherein an effect of the first reflection on a p or s component of a polarized beam in the dual reflection surface means configuration, is canceled by a similar effect in the second reflection on an s or p component, respectively.

17. A method of investigating a sample which is caused to rotate about an axis which is not exactly normal to a surface thereof such that said surface wobbles as said sample rotates, with an electromagnetic beam, said method serving to reduce an effect of said wobble, comprising:
   a) providing a system for investigating a sample comprising:
     a dual reflection surface means selected from the group consisting of:
      two separate reflection surfaces; and
      a single element having two reflection surfaces;
configured to provide an output beam in a plane which is rotated by 90 degrees from a locus of an input beam entered thereinto; said dual reflection surface means further serving to substantially compensate any beam polarization effects on a beam polarization state entered by a first beam directing reflection therewithin, by effects of a second beam directing reflection therewithin, the mechanism thereof being that an effect of the first reflection on a p or s component of a polarized beam in the dual reflection surface means configuration, is canceled by a similar effect in the second reflection on an s or p component, respectively;
   a system for causing a sample to rotate about an axis which is not exactly normal to a surface thereof;
   a spherical mirror; and
   a detector;
   such that a source of a spectroscopic beam of electromagnetic radiation directs an input spectroscopic beam of electromagnetic radiation to enter said dual reflection surface means and exit therefrom in a plane which is rotated by 90 degrees from a locus of the input beam such that said spectroscopic beam of electromagnetic radiation reflects from the surface of a sample while said sample is caused to rotate about an axis which is not normal to said surface of said sample, such that said sample surface wobbles as said sample rotates, and such that said spectroscopic beam of electromagnetic radiation which reflects from a first location on said wobbling sample surface further reflects from said spherical mirror back toward said wobbling sample surface such that said spectroscopic beam of electromagnetic radiation reflects therefrom at a second location thereon and enters said detector;
   b) obtaining data from said detector while said source of spectroscopic beam of electromagnetic radiation directs a beam of spectroscopic electromagnetic radiation along an axis such that said spectroscopic beam of electromagnetic radiation enters said dual reflection-surface means and exits therefrom in a plane which is rotated by 90 degrees, such that said spectroscopic beam of electromagnetic radiation reflects from the surface of a sample which is caused to rotate about an axis not directed normal to the surface of said sample such that said sample surface wobbles as said sample rotates, and such that said spectroscopic beam of electromagnetic radiation which reflects from a first location on said wobbling sample surface further reflects from said spherical mirror back toward said wobbling sample surface such that said spectroscopic beam of electromagnetic radiation reflects therefrom at a second location thereon and enters said detector.

18. A method as in claim 17, in which step a) further comprises providing a polarizer between said source and sample, and an analyzer between said sample and detector and in which the system for investigating a sample provided in step a) is an ellipsometer or polarimeter; and wherein during practice of step b), as the spectroscopic beam of electromagnetic radiation passes through said dual reflection surface means, an effect of the first reflection on a p or s component of a polarized beam in the dual reflection surface means configuration, is canceled by a similar effect in the second reflection on an s or p component, respectively.

19. A method as in claim 17 in which the method further comprises performing at least one selection from the group consisting of:
   storing at least some data provided by said detector in machine readable media;
   analyzing at least some data provided by said detector and storing at least some results of said analysis in machine readable media;
   displaying at least some data provided by said detector;
   analyzing at least some data provided by said detector and displaying at some results of said analysis;
   causing at least some data provided by said detector to produce a signal which is applied to provide a result; and
   analyzing at least some of the data provided by said data detector and causing at least some thereof to produce a signal.

* * * * *